United States Patent [19]
Miyahara et al.

[11] Patent Number: 5,362,445
[45] Date of Patent: Nov. 8, 1994

[54] BIOCHEMICAL ANALYZER AND ATTENUATED TOTAL REFLECTION PRISM CELL USED IN SAID ANALYZER

[75] Inventors: Yuji Miyahara; Toshiko Fujii, both of Hitachi, Japan; Thomas Bührer, Winterthur, Switzerland; Yoshio Watanabe, Hitachi, Japan

[73] Assignee: Hitachi, Ltd., Tokyo, Japan

[21] Appl. No.: 73,640

[22] Filed: May 17, 1993

Related U.S. Application Data

[63] Continuation of Ser. No. 735,876, Jul. 25, 1991, abandoned.

[30] Foreign Application Priority Data

Jul. 27, 1990 [JP] Japan .................................. 2-197930
Aug. 31, 1990 [JP] Japan .................................. 2-231356

[51] Int. Cl.$^5$ ............................................ G01N 21/00
[52] U.S. Cl. .................................. 422/82.09; 356/36; 422/66; 422/67; 422/82.11
[58] Field of Search ............... 422/82.09, 82.11, 66, 422/67; 436/171, 178; 435/808; 356/36; 250/328, 304, 341

[56] References Cited

U.S. PATENT DOCUMENTS

| | | | |
|---|---|---|---|
| 3,287,557 | 11/1966 | Bartz | 356/429 |
| 3,478,206 | 11/1969 | Gaglione | 356/51 |
| 3,486,829 | 12/1969 | Wilks, Jr. | 356/51 |
| 4,158,772 | 6/1979 | Reedy | 356/244 |
| 4,225,228 | 9/1980 | DiMatteo | 356/36 |
| 4,228,192 | 10/1980 | Sanden | 250/339 |
| 4,688,936 | 8/1987 | Reedy | 356/36 |
| 4,841,145 | 6/1989 | Wada et al. | 356/36 |
| 4,906,439 | 3/1990 | Grenner | 422/56 |
| 4,942,134 | 7/1990 | Winefordner | 436/171 |
| 5,118,608 | 6/1992 | Layton et al. | 435/808 |

FOREIGN PATENT DOCUMENTS

| | | | |
|---|---|---|---|
| 0111423 | 7/1982 | Japan | 356/51 |
| 0168143 | 6/1990 | Japan | 422/82.09 |
| 2148024 | 5/1985 | United Kingdom | 356/244 |

OTHER PUBLICATIONS

T. S. Hermann, *The Review of Scientific Instruments*, "A Cell for the Infared Study of Molecules at Low Temperatures"(8/69), pp. 1062–1065.

Martin, *Infared Instrumentation and Techniques*, Elsevier Publishing Co. (1966), pp. 155–169.

Analytical Chemistry, vol. 61, No. 18, Sep. 15, 1989, pp. 2009–2015.

Applied Optics, 27, 1988, pp. 5077–5081.

Proteins at Interfaces, Chapter 23, "Fourier Transformation Infrared Spectro-scopic and Attenuated Total Reflectance Studies of Protein Adsoprtion in Flowing Systems", pp. 362–377.

Applied Spectroscopy, vol. 35, No. 4, 1981, pp. 353–357.

Journal of Colloid and Interface Science, vol. III, No. 2, Jun. 1986, pp. 343–362.

Journal of Biomedical Material Research, vol. 13, (1979), pp. 893–906.

Analytical Letters, 22(9), 1989, pp. 2065–2073.

*Primary Examiner*—James C. Housel
*Assistant Examiner*—Laura E. Collins
*Attorney, Agent, or Firm*—Fay, Sharpe, Beall, Fagan, Minnich & McKee

[57] ABSTRACT

A biochemistry analyzer includes, an attenuated total reflection prism, a sample cell disposed on a surface of the prism, a sample supplier, a device for disposing more objective molecules in the liquid sample to a near portion of the sample which is near the surface of the prism, an infrared light source for generating an infrared light which is transmitted to the attenuated total reflection prism, a detector for detecting the infrared light which is reflected from the prism after the far portion of the sample is solidified, and a computer for calculating signals from the detector. As the objective molecules are gathered near the prism, accuracy of the biochemistry analyzer becomes higher.

12 Claims, 6 Drawing Sheets

BIOCHEMICAL ANALYZER AND ATTENUATED TOTAL REFLECTION PRISM CELL USED IN SAID ANALYZER

This is a continuation application of Ser. No. 07/735,876, filed Jul. 25, 1991, now abandoned.

BACKGROUND OF THE INVENTION

The present invention relates to a biochemical analyzer, and more specifically to a biochemical analyzer for testing blood and an attenuated total reflection prism cell preferably used in this analyzer.

Analysis of biochemical substances such as fluids of living bodies using the infrared spectroscopic method has been discussed in the journal Analytical Chemistry, 61, 1989, pp. 2009-2015. According to the above journal, the glucose concentration in the blood is measured using a general-purpose Fourier transform infrared spectroscopic apparatus in compliance with the attenuated total reflection (ATR) method.

A sample to be measured is introduced into a flow cell which incorporates a cylindrical ATR prism, infrared absorption spectra are measured at room temperature, and the concentration of the glucose component is calculated based on the method of partial least squares.

The above prior art was not satisfactory in regard to correlation of analytical values compared with the colorimetric method using enzymes that is a reference method for glucose analysis, and was not satisfactory in regard to precision of analysis, either. Furthermore, use of the general-purpose Fourier transform infrared spectroscope requires manual operation for pouring samples, washing the ATR prism and effecting the calibration. When employed in general hospitals, therefore, the biochemical analyzer was very clumsy to use.

In the conventional ATR prism used for the biochemical analyzers, in particular, attention has not been given in regard to the adsorption of blood cells and proteins on the surface of the attenuated total reflection prism when the sample consists, for example, of blood. Therefore, the life of the attenuated total reflection prism was short due to the adsorption of blood components. The attenuated total reflection prism is so expensive that a deteriorated one must be used again after polishing it, making the biochemical analyzer very clumsy to use.

The biochemical analysis based on the attenuated total reflection which involves the above-mentioned problems has been described in, for example, Applied Optics, 27, 1988, pp. 5077-5081.

Furthermore, the following examples have been known in which a substance having a high refractive index or a high molecular membrane is interposed between the surface of the ATR prism and the sample.

Japanese Patent Publication No. 55-500589 of translated version in PCT application.

Proteins at Interfaces, Chapter 21, "Adsorption of Fibronectin to Polyurethane Surface: Fourier Transform Infrared Spectroscopic Studies", pp. 324-338.

Proteins at Interfaces, Chapter 23, "Fourier Transformation Infrared Spectroscopic and Attenuated Total Reflectance Studies of Protein Adsorption in Flowing Systems, pp. 362-377.

Applied Spectroscopy, Vol. 35, No. 4, 1981, pp. 353-357.

Journal of Colloid and Interface Science, Vol. 111, No. 2, June, 1986, pp. 343-362.

Journal of Biomedical Materials Research, Vol. 13, 1979, pp. 893-906.

Analytical Letters, 22(9), 1989, pp. 2065-2073.

However, the above conventional examples have a defect in that the membrane becomes thick and spectrum signals detected via the ATR become so weak that satisfactory precision is not obtained.

SUMMARY OF THE INVENTION

An object of the present invention is to provide a biochemical analyzer which is capable of high precision analysis of biochemical substances, the analyzer having means which distributes the object substance in the liquid sample so as to be thicker toward the surface of the ATR prism in the sample medium in order to obtain stronger spectrum signals that are detected by the ATR prism and to improve detection precision.

Concretely speaking, means for cooling the object substance in the sample is provided on the surface of the ATR prism in order to cool it in a manner that the liquid sample successively coagulates starting at a portion separated away from the surface of the ATR prism toward the surface of the ATR prism. Therefore, the object substance in the liquid sample is distributed being deviated toward the portion of the sample that is coagulated last; i.e., the concentration of the object substance becomes the greatest in a portion of the sample that comes last in contact with the surface of the ATR prism. Therefore, the spectrum signals detected by the ATR prisms have an increased magnitude contributing to improving the precision of detection.

Speaking further concretely, provision is made of a molecule separation membrane which permits the object substance in the sample to be permeated but interrupts the passage of undesired substances such as proteins and blood cells on the surface of the ATR prism. Therefore, the object substance only of the sample is distributed, being deviated on the surface of the ATR prism, whereby relatively great spectrum signals of object substance are obtained contributing not only to improving the precision of detection but also preventing the proteins and blood cells from adhering on the surface of the ATR prism, enabling the life of the ATR prism to be lengthened and high precision of detection to be maintained for extended periods of time.

DETAILED DESCRIPTION OF THE PREFERRED EMBODIMENTS

The present invention is concerned with a biochemical analyzer that has a source of infrared light, an infrared spectrometer, and an ATR prism cell into which the sample will be poured, and that detects the spectra absorbed by the liquid sample poured into the ATR prism cell, wherein provision is made of means which distributes the object substance in the liquid sample so as to be thicker toward the surface of the ATR prism in the sample medium.

Figure 1:
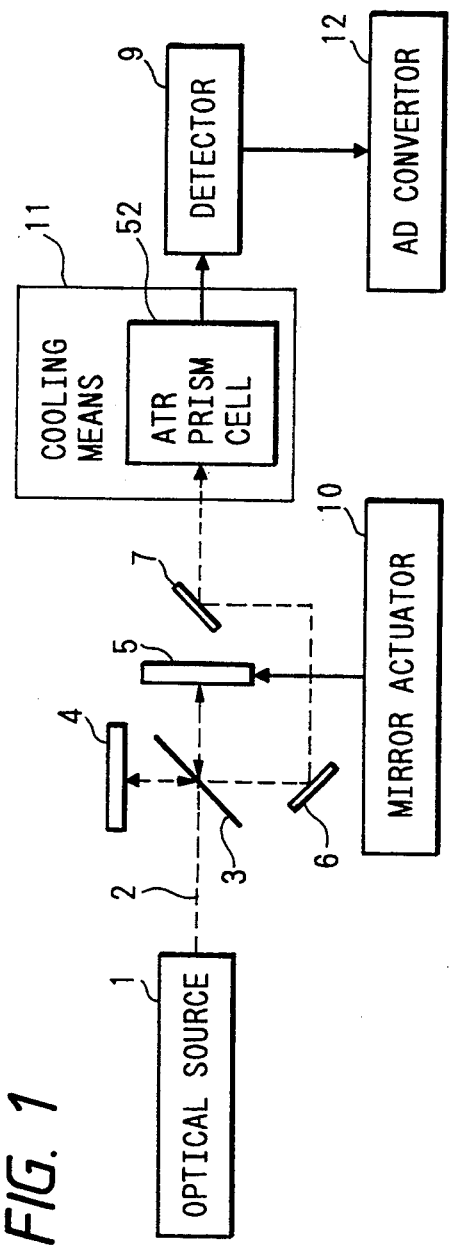
FIG. 1 is a schematic view showing an embodiment of a biochemical analyzer of the present invention.

FIG. 1 illustrates a biochemical analyzer in which the above-mentioned means for deviated distribution is constituted by means that cools the liquid sample. This constitution will now be described in conjunction with the drawings.

In FIG. 1, the infrared light 2 emitted from an optical source 1 is divided by a half mirror 3 into a component heading toward a fixed mirror 4 and a component heading toward a movable mirror 5. These components are reflected by the fixed mirror 4 and the movable mirror 5, respectively, and return again to the half mirror 3 where they are synthesized together. The synthesized light is reflected by mirrors 6 and 7, and falls on an ATR prism cell 52.

The infrared light 2 incident on the ATR prism cell 52 is partly absorbed by the sample and is detected by a detector 9.

The detect signal is subjected to AD conversion through an AD converter 12.

The movable mirror 5 is driven by a mirror actuator 10, and the light reflected thereby interferes with the light that is reflected by the fixed mirror 4 to form an interferogram.

The ATR prism cell is installed in a cooling means 11 and analyzes the sample under the cooled condition.

Figure 2:
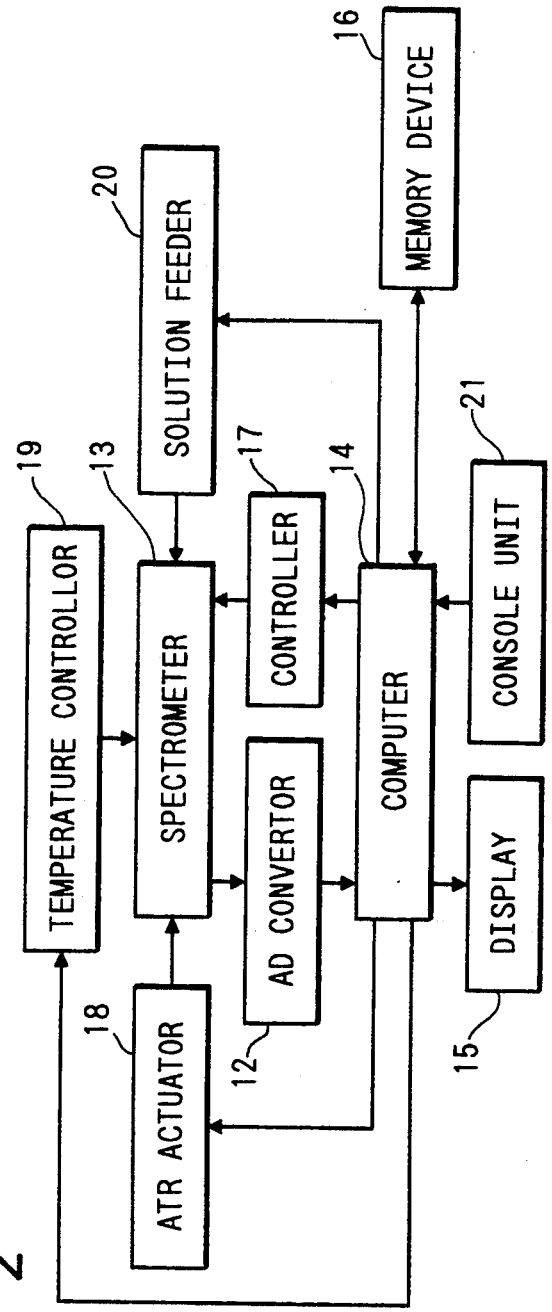
FIG. 2 is a schematic view showing a control system of the biochemical analyzer of the present invention.

FIG. 2 is a schematic view for illustrating a control system in the analyzer of the present invention.

The absorption spectrum signals of the sample measured by a spectrometer 13 are input via the AD converter 12 to a computer 14 which performs operations such as calculating the peak areas, calculating the concentrations and the like. These results and the necessary data based thereupon are output to a display 15.

To the computer is connected a memory device 16 which stores the measured absorption spectra and calculated results such as areas, strengths and concentrations.

Operation of the movable mirror 5 of the spectrometer is controlled by a controller 17. The ATR prism cell 52 is carried by an ATR actuator 18. Here, the sequence of ATR carriage is set by the computer 14.

The cooling temperature of the sample being measured is controlled by a temperature controller 19 based on an instruction from the computer 14. The washing solution necessary for washing the ATR prism and the standard solution used for the calibration are sent from the solution feeder 20.

The operations for analyzing the sample, washing the analyzer, effecting the calibration and controlling the temperature of the cooling means can be performed by an operator by simply inputting necessary data via a console unit 21.

Figure 3:
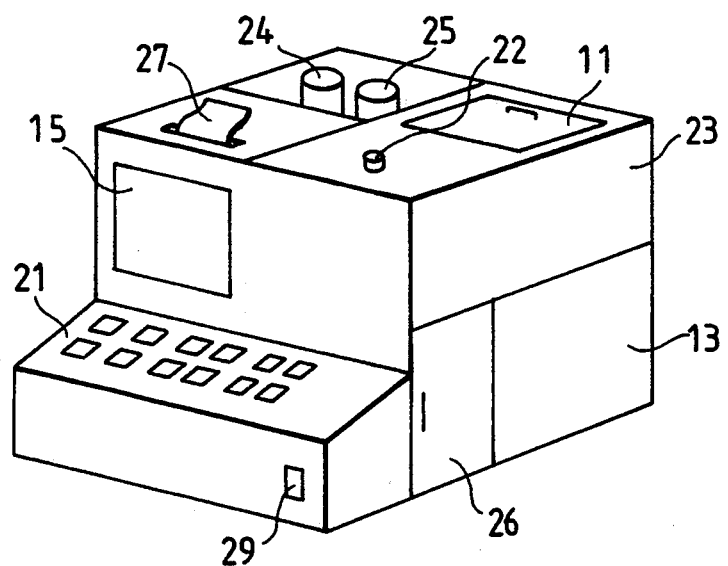
FIG. 3 is a perspective view showing the biochemical analyzer of the present invention.

FIG. 3 is a perspective view showing the biochemical analyzer of the present invention.

The sample to be measured is poured onto the ATR prism cell through a sample pouring port 22, and is carried into the cooling means 11 by an ATR carrier contained in one portion 23 of a housing of the biochemical analyzer. The cooling means 11 is formed integrally with an ATR prism cell-mounting portion of the spectrometer 13 that is disposed thereunder, enabling the infrared absorption spectra of the sample to be measured under the cooled condition.

The solution for washing the ATR prism and the standard solution are contained in the containers 24 and 25, respectively, and waste solutions after use are collected into a waste solution container placed in another portion 26 of the analyzer housing.

The concentrations of components of the sample measured are calculated by the computer and are displayed on a display 4, and are further output as required to a printer 27. The items of measurement, sample numbers and the like are input through the console unit 21.

Figure 4:
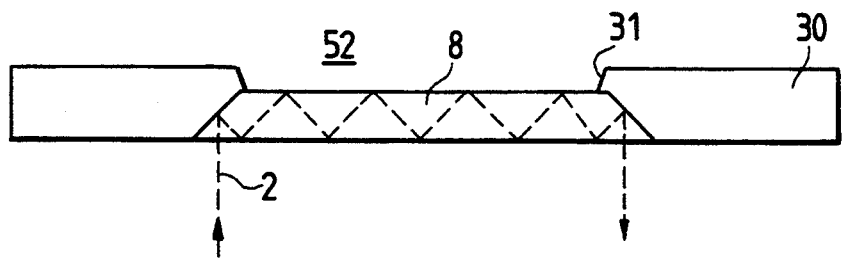
FIG. 4 is a sectional view showing an ATR prism cell used in the embodiment of the biochemical analyzer of FIG. 1.

FIG. 4 is a sectional view of the ATR prism cell 52 consisting of an ATR prism 8 and a support member 30 which has a step 31.

The ends of the ATR prism 8 are tilted at an angle of 45 degrees such that the infrared light 2 that is incident goes out while repeating the multiple reflection. The prism 8 is firmly held by the support member 30 which has the step formed like a frame to constitute the ATR prism cell 52 that holds the sample solution on the upper surface of the ATR prism 8.

Figure 5:
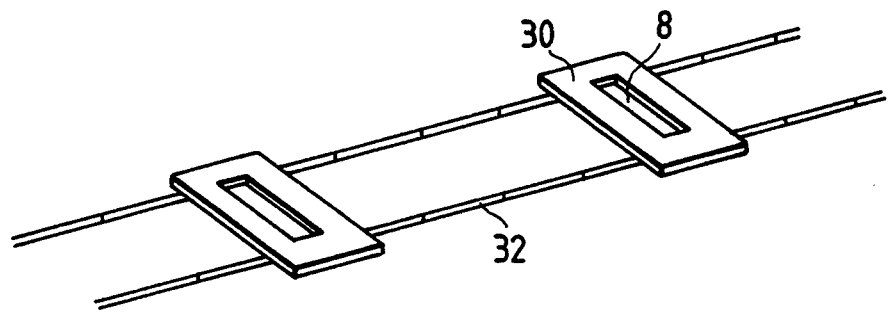
FIG. 5 is a perspective view showing means for carrying the ATR prism cell.

ATR prism cell 52 constituted by the ATR prism 8 and the ATR support member 30 is firmly supported on a carrying system 32 in the form of a flexible belt or a chain as shown in FIG. 5, and is carried into the cooling means 11. A plurality of ATR prism cells can be firmly held by the carrying system 32 so as to be successively carried.

Figure 6:
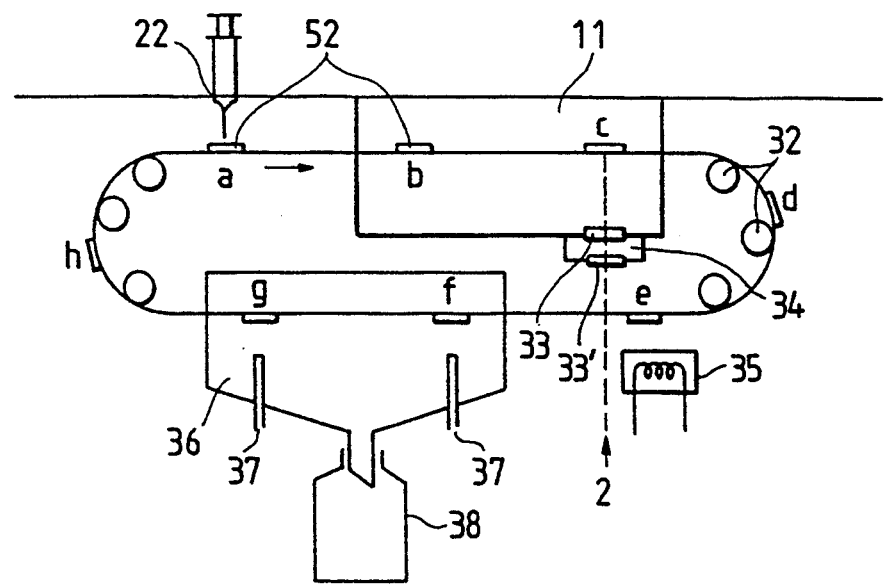
FIG. 6 is a schematic view showing an embodiment of a biochemical analyzer having a carrying system of the ATR prism cell of the present invention.

FIG. 6 is a schematic view of the analyzer equipped with the carrying system.

A sample to be measured is poured from the sample pouring port 22 into the ATR prism cell 52 located at a position a of the carrying system 32. The ATR prism cell in which the sample is poured is carried to a position b in the cooling means 11 as the carrying system 32 is driven in the direction the arrow. The ATR prism cell 52 cooled to a predetermined temperature at the position b is carried to a position c where it is irradiated with the infrared ray 2 from the lower direction to measure the absorption spectra.

The infrared light 2 is permitted to be incident via duplex windows 33 and 33' that are partitioned from each other. A gap 34 between the duplex windows 33 and 33' at vacuum or is filled with a dry gas. The duplex windows 33 and 33' are thermally insulated, so that the water vapor will not condense on the surface of the window 33 when cooled and so that the window will not be thereby clouded up with the water vapor.

After being measured, the sample in the ATR prism cell 52 that has been frozen is melted at a position d. The sample that is not fully melted is heated by a heater 35 at a position e until it is completely melted. The ATR prism cell is carried into a washing portion 36 where it is automatically washed with the washing solution injected from the washing solution injection ports 37 at positions f and g. The washing solution after washing is recovered in a waste solution container 38.

The ATR prism cell 52 is dried at a position h and is used again for measurement. The number of analyses can be increased by providing more than one ATR prism cell 52.

Figure 7:
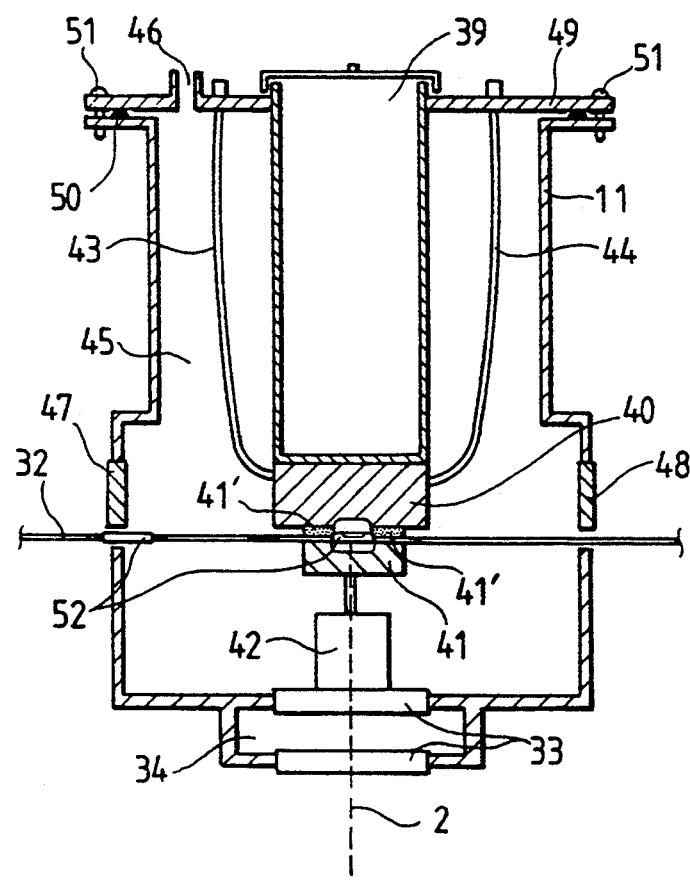
FIG. 7 is a sectional view showing a cooling means for the ATR prism cell used in the biochemical analyzer of the present invention.

When the measurement is to be taken at very low temperatures using a mixture consisting of dry ice and an alcohol or liquid nitrogen or liquid helium as a cooling medium of the cooling means 11, there can be employed the cooling means 11 that is shown in FIG. 7.

The bottom of a cooling medium container 39 such as the Dewar vessel filled with the cooling medium is formed by a block 40 made of a good heat conductor such as copper, and the ATR prism cell 52 is cooled, being sandwiched by the block 40 and a holding plate 41 via a heat insulating material 41' such as a foamed styrene or a foamed urethane. In the block 40 are buried a temperature sensor 43 and a heater 44 for temperature control in order to control the temperature of the block.

The block 40 which is cooled by the cooling medium 39 is thermally insulated from the holding plate 41 and the sample cell 52, and is maintained at a low temperature compared with the holding plate 41 and the sample cell 52. On the other hand, the sample placed on the sample cell 52 is cooled via the layer of dry gas surrounded by a heat insulating material 47' provided under the block 40. Therefore, the temperature of the sample becomes lower on the side of the block 40 which is separated away from the ATR prism 8 than on the side of the ATR prism. Hence, the sample placed on the ATR prism 8 coagulates successively starting at a place away from the ATR prism toward the ATR prism 8.

In effect, the object substance to be measured coagulates while being deviated toward the side of the ATR prism 8, and the distribution of the object substance in the sample becomes denser toward the side of the ATR prism 8. Therefore, the ATR prism 8 makes it possible to obtain very dense absorption spectra of the object substance. The holding plate 41 moves up and down being driven by a motor 42.

Furthermore, the dry gas has always been fed from a gas feed port 46 into internal space 45 of the cooling means 11 preventing the water from condensing on the surfaces of the ATR prism 8 of the ATR prism cell 52 and the duplex windows 33.

The ATR prism cell onto which the sample to be measured is poured is carried by the carrying means 32 into or out of the cooling means 11 by opening the door 47 or the door 48 of the cooling means 11. Further, the upper cover 49 of the cooling means is fitted thereto via a packing 50 so that it can be opened as required.

Figure 8:
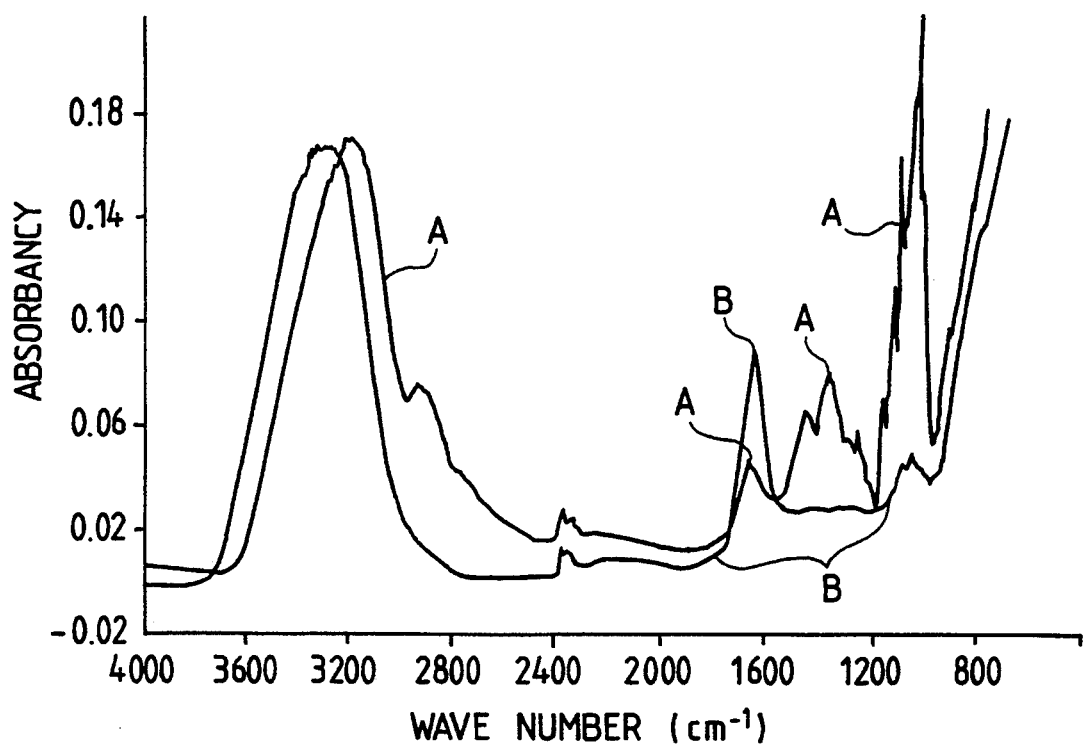
FIGS. 8 and 9 are schematic views showing infrared absorption spectra measured by the biochemical analyzer of the present invention.

FIG. 8 shows the infrared absorption spectra of a glucose aqueous solution measured by using the analyzer of the present invention which is equipped with the cooling means that is shown in FIG. 7.

FIG. 8 shows in comparison the case where an aqueous solution having a glucose concentration of 0.5 mole is measured at a temperature of about 147° K. (curve A) and at room temperature (curve B).

When peak areas are compared over 950 to 1180 cm$^{-1}$ where glucose peaks increase as will be obvious from the drawing, the peak area of glucose at a low temperature is more than ten times as great as that at room temperature, from which it will be understood that the sensitivity for measuring the biochemical substances becomes very great at low temperatures.

Figure 9:
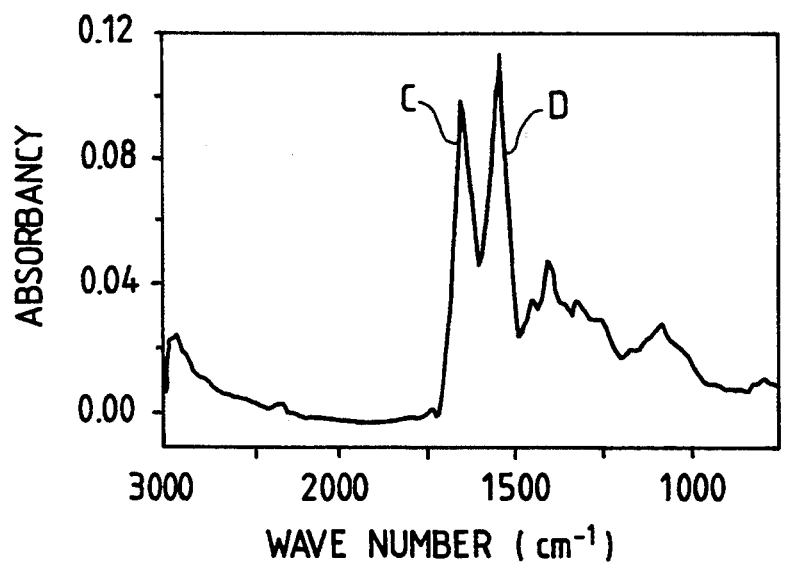

FIG. 9 shows the infrared absorption spectra of the blood measured at room temperature.

In FIG. 9, the peaks C and D are those of amide I and amide II of a protein. Glucose exhibits a broad peak at around 1035 cm$^{-1}$.

Here, by utilizing the fact that the peak area in the absorption spectra measured by the aforementioned measuring apparatus has a proportional relationship relative to the concentration of the measured sample, it is possible to prepare a calibration curve from the peak area of glucose of a known concentration over a range of 950 to 1180 cm$^{-1}$ in order to easily find the concentration of unknown glucose using the above calibration curve.

Figure 10:
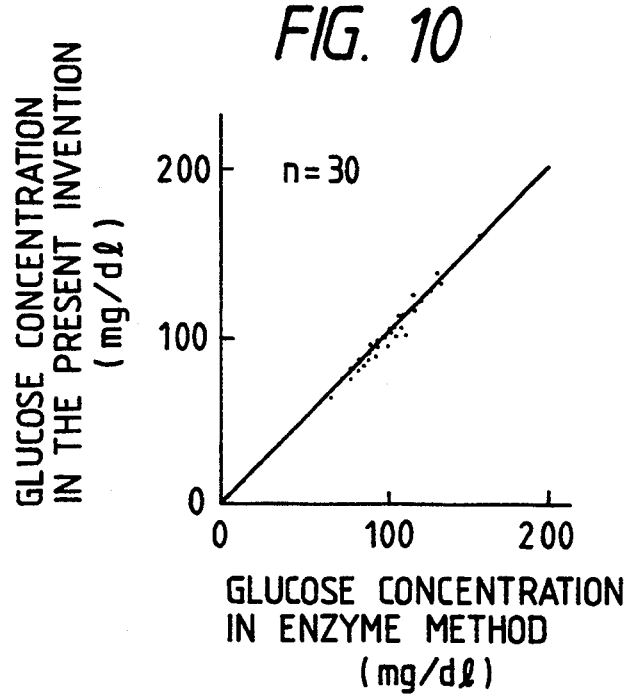
FIG. 10 is a graphical view showing a relation of the glucose concentrations measured by the biochemical analyzer of the present invention and the conventional enzyme method.

FIG. 10 is a graph showing a correlation between a glucose concentration measured using the biochemical analyzer of the present invention and a glucose concentration measured by the conventional colorimetric method using an enzyme.

It will be understood that the correlation coefficient between them is 0.97 and the measured results are in good agreement between them.

Figure 11:
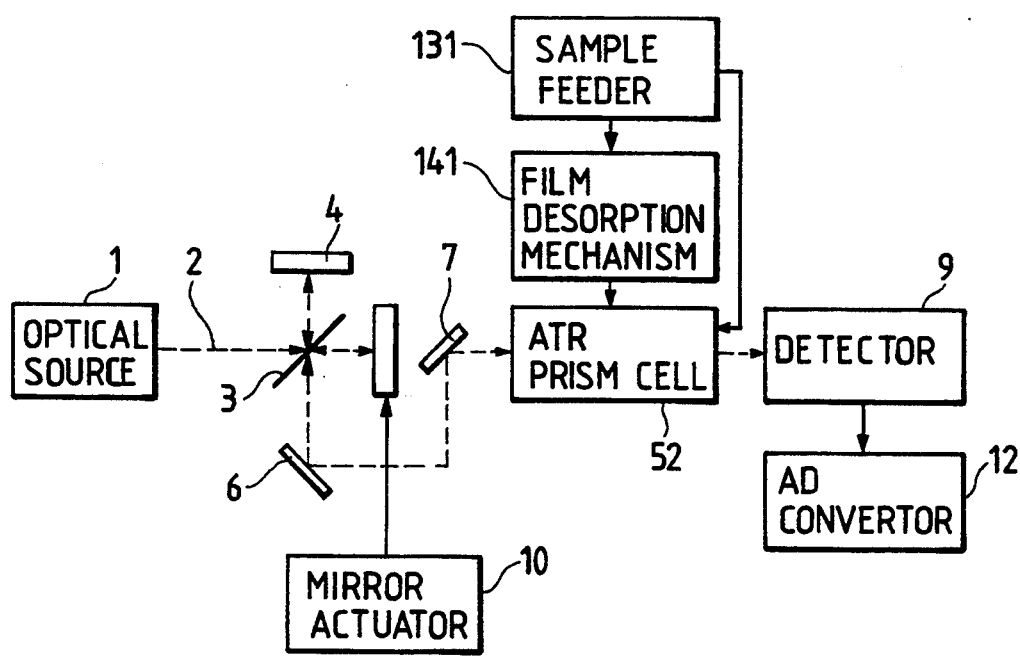
FIG. 11 is a schematic view showing another embodiment of the biochemical analyzer in the present invention.

Next, another embodiment of the present invention will be described in detail. FIG. 11 shows the constitution of the biochemical analyzer according to another embodiment of the present invention. The infrared light 2 emitted from the optical source 1 is decomposed by a half mirror into a component directed to a fixed mirror 4 and a component directed to a movable mirror 5. These components are synthesized again by the half mirror 3. The synthesized light is reflected by mirrors 6 and 7, and falls on the ATR prism cell 52. The infrared light is partly absorbed by the sample in the ATR prism and is detected by a detector 9. The signal of the detector is subjected to the AD conversion through an AD converter 12. The movable mirror 5 is actuated by a mirror actuator 10, and the light reflected thereby interferes with the light reflected by the fixed mirror 4 to form an inteferogram. The sample is introduced onto the ATR prism by a sample feeder 131 and a film desorption mechanism 141, or by the sample feeder 131.

Figure 15:
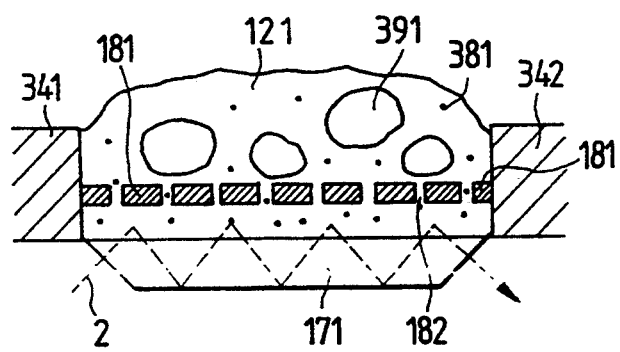

The feature of the present invention resides in the provision of a molecule separation membrane which is provided between the surface of the ATR prism and the sample, and which has the constitution as shown in FIG. 15 wherein reference numeral 181 denotes a thin molecule separation membrane composed of a high molecular material having a high hydrophilic property and having pore 182. The blood 121 which is a sample is introduced onto the membrane 181 that is placed on the surface of the ATR prism 171 directly or to maintain a gap. Low molecular components 381 such as glucose, uric acid, urea and the like contained in the blood, pass through pores 182 in the membrane 181 together with the water which is a medium thereof, and reach the ATR prism 171. Proteins and blood cells 391 contained in the blood are too big to pass through the pores 182 in the membrane 181 and stay separated on the membrane 181. According to the present invention, low molecular substances only, which are the object components such as glucose and the like, are densely distributed in the path through which the light falls on the sample from the ATR prism, and the analysis is carried out maintaining good precision without being interrupted by proteins. Moreover, the proteins and blood cells do not come in direct contact with the ATR prism; i.e., proteins are not adsorbed on the surface of the ATR prism and the life of the prism can be lengthened.

Figure 14:
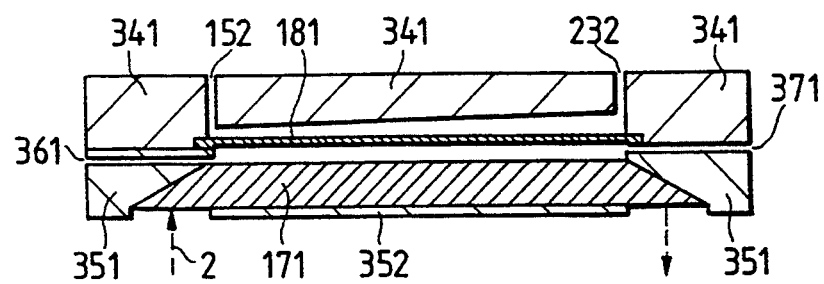

The embodiment of the present invention which uses the above membrane 181 will now be described in detail. FIG. 14 is a sectional view of the first embodiment of the present invention. The cellulosic dialytic membrane 181 which is 0.5 mm thick is sandwiched by jigs 341 and 351 along its four sides and is disposed on the ATR prism 171 maintaining a gap of 2 mm. A flow path is formed in the jig 351, and distilled water is poured through a water pouring port 361 thereof so as to fill the gap between the ATR prism 171 and the membrane 181. The water pouring port 361 and the water discharge port 371 are closed after the gap is filled with the distilled water. After the distilled water has been poured, the sample is poured onto the membrane 181 through a sample pouring port 152 formed in the jig 341. Low molecular substances such as urea, glucose and uric acid contained in the sample are separated into the water from the sample that has passed through the membrane 181 due to the concentration gradient of sample and water. The spectra of water containing low molecular substances that have passed through the membrane on the prism 171 are measured by the ATR prism 171.

Figure 12:
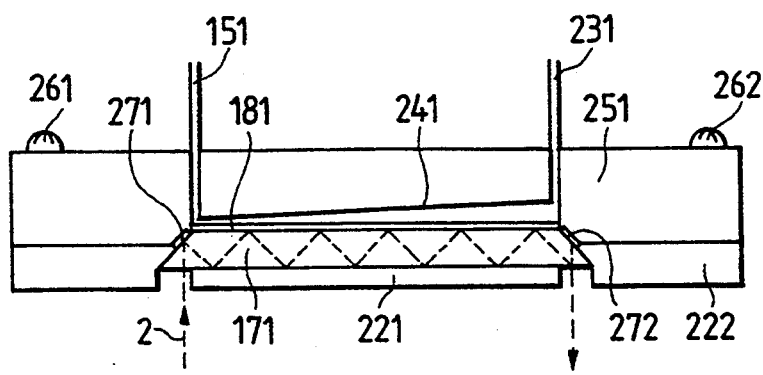

FIG. 12 is a sectional view showing another embodiment of the present invention. One surface of a polysulfonic porous support membrane (0.5 mm thick) having a large porosity in the surface is treated with plasma to choke the pores so as to have diameters of about 15 mm, in order to obtain a composite membrane having a very thin membrane (1 $\mu$m thick) that contributes to separating proteins. The choked surface is permitted to come into light contact with the surface of the ATR prism 171, and the sample is introduced onto the non-choked surface through the sample pouring port 151. The sample flow path on the ATR prism 171 is inclined as at 241 to prevent the generation of bubbles. The sample introduced from the side of the non-choked surface quickly permeates into the porous portions of the membrane 181 and is uniformly dispersed on the very thin membrane that is formed under the porous portions. The low molecular substances such as glucoses contained in the sample pass through the very thin membrane together with the water due to the capillarity and reach the prism 171. In this case, high molecular substances such as proteins in the sample are not permitted to pass through the very thin membrane and stay on the porous portion being separated. The ATR prism 171 measures the spectra of the water containing low molecular substances that have passed through on the prism 171. After measurement, the washing solution is poured through the sample pouring port 151 in order to discharge the sample from the sample discharge port 231 together with the washing solution.

In FIG. 12, reference numeral 251 denotes a material forming the flow path, 261 and 262 denote screws, 271 and 272 denote seals, and 221 and 222 denote ATR prism support members.

In addition to the above-mentioned membrane 181 of FIG. 12, there can be used the following membrane. That is, the ATR prism 171 is directly dip-coated or spin-coated with a mixture solution consisting of cellulose, glutaraldehyde and albumin of cow serum and, then, the solvent is dried to form a membrane which is 2 $\mu$m thick. N Terminals of proteins contained in the sample react with CHO groups of glutaraldehyde in the membrane to form Schiff bases which are chemically adsorbed. The sample from which the proteins are removed is permitted to pass through onto the prism 171. Furthermore, the albumin concentration may be increased in the mixture solution which is the starting material of the membrane, in order to form on the prism a membrane in which albumin is chemically adsorbed on the Schiff base of glutaraldehyde; i.e., a membrane 181 having good water permeability is formed which works not as a chemical adsorption film but as a physical filter, enabling the low molecular components only to pass through onto the prism 171 but separating the proteins to stay on the membrane 181.

Figure 13:
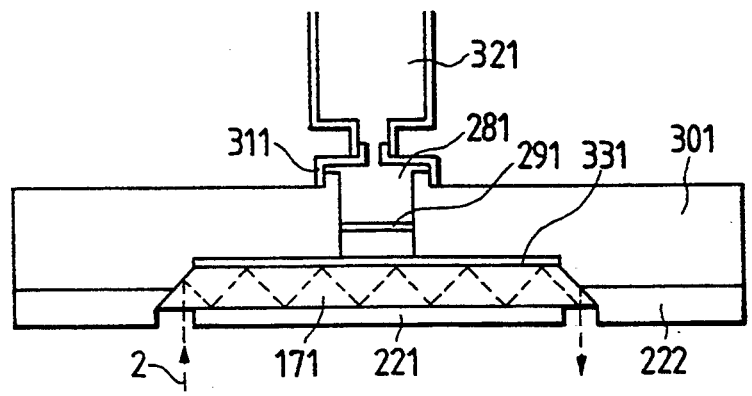
FIGS. 13, 14 and 15 are sectional views showing ATR prism cells used in further embodiments of the biochemical analyzer of FIG. 11.

FIG. 13 is a sectional view of a further embodiment of the present invention. A membrane 291 is composed of a polyimide, a polysulfone or a polyether sulfone having a porous diameter of 15 nm, and serves as an ultrafilter. The ultrafilter is a composite membrane consisting of an active layer having a thickness of smaller than 1 $\mu$m and a porous layer having a thickness of about 0.5 mm. To take the measurement, the ultrafilter is so set that the sample is introduced directly onto the active layer. After the sample is introduced onto the membrane 291, pressure is exerted on the sample from a syringe 321, substances (proteins, blood cells, etc.) having sizes greater than 15 nm in the sample are removed by the membrane under the application of pressure, and the sample from which the proteins are removed is permitted to drop on a sample spreading layer 331. The sample spreading layer 331 consists of a fibrous material having good water permeability such as a filtering paper or a porous film having a thickness of smaller than 0.5 mm, and works to quickly spread the sample dropped thereon on the prism. The sample held by the spreading layer 331 is measured for its absorption spectra by the ATR prism 171.

In FIG. 13, reference numeral 281 denotes a sample port, 221 and 222 denote ATR prism support members, and 301 denotes a membrane support member.

According to the embodiments shown in FIGS. 12 to 15 as described above, the membrane 181 or 291 is provided between the surface of the ATR prism and the sample to permit the passage of low molecular object substances but to block the passage of high molecular substances such as proteins and blood cells that interrupt measurement.

Therefore, the object substances to be measured are distributed so as to be denser toward the surface of the ATR and increased absorption spectra are obtained, improving precision of the biochemical analyzer, preventing adhesion of substances that hinder measurement to the ATR prism and ensuring high-precision measurement for extended period of time.

We claim:

1. A biochemistry analyzer for analyzing an objective substance in a liquid sample, comprising:
   a housing including therein:
      an attenuated total reflection prism; a sample prism cell disposed on a side surface of the attenuated total reflection prism; a sample supplying means for supplying a liquid sample to the sample prism cell; distributing means in said sample prism cell for distributing an objective substance in the liquid sample to concentrate the objective substance at the side surface of the prism by solidifying the liquid sample in the sample prism cell with solidifying means external to the sample prism cell; an infrared light source for transmitting infrared light through the objective substance to be reflected from the attenuated total reflection prism; and a detector for detecting the infrared light which is reflected from the attenuated total reflection prism after the liquid sample is solidified, and for providing absorption spectrum data of the detected infrared light with respect to the objective substance and the liquid sample; and a computer for receiving the absorption spectrum data from the detector and for calculating the detected absorption spectrum from the absorption spectrum data.

2. A biochemistry analyzer as defined in claim 1, wherein said solidifying means includes cooling means for solidifying the liquid sample from a fist portion of the liquid sample to a second portion of the liquid sample, said second portion of the liquid sample being in direct contact with said side surface of the attenuated total reflection prism so as to distribute more of said objective substance in the liquid sample toward said side surface of the attenuated total reflection prism.

3. A biochemistry analyzer as defined in claim 2, further comprising a double window on the cooling means which passes the infrared light from the infrared light source to the prism.

4. A biochemistry analyzer as defined in claim 2, further comprising a heating means for heating the sample prism cell after the detector detects the absorption spectrum of the liquid sample, and a washing means for washing the sample prism cell after the heating means heats the sample prism cell.

5. A biochemistry analyzer as defined in claim 2, further comprising a Dewar bottle for adding a cooling medium, disposed on or over the sample cell.

6. A biochemistry analyzer as defined in claim 1, wherein said distributing means includes a film for separating the objective substance from nonobjective substances by weight.

7. A biochemistry analyzer as defined in claim 6, wherein a region defined between said film and said prism contains distilled water.

8. A biochemistry analyzer as defined in claim 6, wherein said film is a porous film through which is passed the objective substance in order to prevent such passage of the nonobjective substances.

9. A biochemistry analyzer as defined in claim 6, wherein said film is a filter having small holes of diameter about 15 nm, said filter including an activated layer and a porous layer.

10. A biochemistry analyzer as defined in claim 1, wherein the distributing means includes separation means for separating the objective substance from nonobjective substances contained in the liquid sample.

11. A biochemistry analyzer for analyzing an objective substance in a liquid sample, comprising:

a housing including therein:

an attenuated total reflection prism; a sample prism cell disposed on a side surface of the attenuated total reflection prism; a sample supplying means for supplying a liquid sample to the sample prism cell; distributing means for distributing an objective substance in the liquid sample in conjunction with a cooling means external to the sample prism cell for freezing the liquid sample progressively from a first portion of the liquid sample to a second portion of the liquid sample, said second portion of the liquid sample being in direct contact with said side surface of the attenuated total reflection prism so as to distribute more of the objective substance in the liquid sample toward the side surface of the attenuated total reflection prism; an infrared light source for transmitting infrared light through the objective substance to be reflected from the attenuated total reflection prism; and a detector for detecting the infrared light which is reflected from the attenuated total reflection prism after the second portion of the liquid sample is frozen, and for providing an output signal representative of the detected infrared light; and a computer for receiving and analyzing the signal from the detector.

12. A biochemistry analyzer as defined in claim 11, wherein said distributing means includes separation means, disposed in the sample prism cell, for separating the objective substance from nonobjective substances contained in the liquid sample.

* * * * *